(12) United States Patent
Urtti et al.

(10) Patent No.: US 6,183,771 B1
(45) Date of Patent: Feb. 6, 2001

(54) TRANSDERMAL COMPOSITIONS CONTAINING LEVOSIMENDAN

(75) Inventors: Arto Urtti, Kuopio; Jouni Hirvonen, Vantaa; Lasse Lehtonen, Espoo; Saila Antila, Helsinki, all of (FI)

(73) Assignee: Orion Corporation, Espoo (FI)

( * ) Notice: Under 35 U.S.C. 154(b), the term of this patent shall be extended for 0 days.

(21) Appl. No.: 09/214,295

(22) PCT Filed: Jun. 26, 1997

(86) PCT No.: PCT/FI97/00412

§ 371 Date: Mar. 23, 1999

§ 102(e) Date: Mar. 23, 1999

(87) PCT Pub. No.: WO98/01111

PCT Pub. Date: Jan. 5, 1998

(30) Foreign Application Priority Data

Jul. 5, 1996 (GB) .................................................. 9614098

(51) Int. Cl.[7] .............................. A61F 13/02; A61K 9/70; A61K 9/14
(52) U.S. Cl. .......................... 424/449; 424/448; 424/484; 424/486
(58) Field of Search ..................................... 424/402, 448, 424/449, 484, 486; 514/846

(56) References Cited

FOREIGN PATENT DOCUMENTS

| 413 487 | 2/1991 | (EP) . |
|---|---|---|
| 565 546 | 3/1995 | (EP) . |
| 0 565 546 B1 * | 3/1995 | (EP) . |
| 92/21334 | 12/1992 | (WO) . |
| 92/21338 | 12/1992 | (WO) . |
| 93/21921 | 11/1993 | (WO) . |

OTHER PUBLICATIONS

Sandell, E.–P. et al., "Pharmacokinetics of Levosimendan in Healthy Volunteers and Patients with Congestive Heart Failure", *Journal of Cardiovascular Pharmacology* 26(Suppl. 1), 1995, 57–62.

* cited by examiner

*Primary Examiner*—Thurman K. Page
*Assistant Examiner*—S. Howard
(74) *Attorney, Agent, or Firm*—Finnegan, Henderson, Farabow, Garrett & Dunner, L.L.P.

(57) ABSTRACT

Transdermal administration of levosimenden or (–)-[[4-(1,4,5,6-tetahydro-4-methyl-6-oxo-3-pyridazinyl)phenyl)hydrazono]propanedinitrile or a pharmaceutically acceptable salt thereof is disclosed. Transdermal preparations of levosimenden can be in the form of e.g. ointment, emulsion, lotion, solution, gel, cream, patch or transdermal delivery device including iontophoretic device.

12 Claims, No Drawings

TRANSDERMAL COMPOSITIONS CONTAINING LEVOSIMENDAN

TECHNICAL FIELD

The invention relates to transdermal preparations containing as an active ingredient levosimendan or a pharmaceutically acceptable salt thereof and to a method of treating heart failure by transdermally administering levosimendan or a pharmaceutically acceptable salt thereof.

BACKGROUND OF THE INVENTION

Levosimendan, which is the (−)-enantiomer of [[4-(1,4,5,6-tetrahydro-4-methyl-6-oxo-3-pyridazinyl)phenyl]hydrazono]propanedinitrile (I), and the method for its preparation is described e.g. in EP 565546 B1. Levosimendan is potent in the treatment of heart failure and has significant calcium dependent binding to troponin. The use of levosimendan in the treatment of myocardial ischemia is described in WO 93/21921. Pharmacokinetics of levosimendan in man after i.v. and oral dosing is described in Sandell, E.-P. et al., J. Cardiovasc. Pharmacol., 26(Suppl.1), S57–S62, 1995.

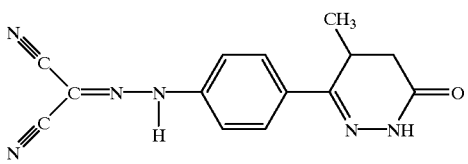

It has now been found that therapeutically effective serum levels of levosimendan can be achieved by administering levosimendan transdermally. Transdermal delivery of levosimendan provides a safe method for administering levosimendan to a patient at a desired steady rate.

SUMMARY OF THE INVENTION

The present invention provides a transdermal preparation comprising as therapeutically active ingredient (−)-[[4-(1,4,5,6-tetrahydro-4-methyl-6-oxo-3-pyridazinyl)phenyl]hydrazono]propanedinitrile or a pharmaceutically acceptable salt thereof.

The present invention also provides the use of (−)-[[4-(1,4,5,6-tetrahydro-4-methyl-6-oxo-3-pyridazinyl)phenyl]hydrazono]propanedinitrile or a pharmaceutically acceptable salt thereof in the manufacture of a medicament for transdermal administration of (−)-[[4-(1,4,5,6-tetrahydro-4-methyl-6-oxo-3-pyridazinyl)phenyl]hydrazono]propanedinitrile or a pharmaceutically acceptable salt thereof.

Furthermore the present invention provides a method for treating heart failure comprising administering transdermally to a subject in need of such treatment an therapeutically effective amount of (−)-[[4-(1,4,5,6-tetrahydro-4-methyl-6-oxo-3-pyridazinyl)phenyl]-hydrazono]propanedinitrile or a pharmaceutically acceptable salt thereof.

DETAILED DESCRIPTION

The transdermal administration of levosimendan or a pharmaceutically acceptable salt thereof can be accomplished for example: (i) by mixing the therapeutically active compound or a pharmaceutically acceptable salt thereof with suitable pharmaceutically acceptable carriers and optionally skin penetration enhancers to form preparations such as ointments, emulsions, lotions, solutions, creams, gels or the like, where preferably a fixed amount of said preparation optionally covered with an impermeable backing layer is to be applied onto a predetermined area of the skin or (ii) by incorporating the therapeutically active substance into patches or transdermal delivery systems according to known technology.

The preparation of suitable transdermal delivery systems is described e.g. in WO 92/21334, WO 92/21338 and EP 413487. Such system may comprise (a) a drug impermeable backing layer and (b) an adhesive layer that fixes the bandage to the skin, wherein the drug is dispersed in the adhesive layer. Alternatively, the system may comprise (a) a drug impermeable backing layer, (b) an adhesive layer and (c) a matrix layer preferably made of a polymer material in which the drug is dispersed. The rate at which the drug is released from the device is here controlled by the polymer matrix. The system may also comprise (a) a drug impermeable backing layer, (b) an adhesive layer, (c) a drug permeable membrane sealed to one side of said backing layer as to define at least one drug reservoir compartment therebetween and (d) a drug or composition thereof within said drug reservoir. In this case the drug in the reservoir is usually in liquid or gel form. The drug permeable membrane controls the rate at which the drug is delivered to the skin.

Iontophoretic transdermal delivery systems according to known technology can also be used in the transdermal delivery of levosimendan. Term "iontophoresis" means using small electric current to increase trans-dermal permeation of charged drugs. The method is reviewed in e.g. Burnette R., Iontophoresis. In Transdermal Drug Delivery, pp. 247–292, Eds. Guy, R. and Hadgraft, J., Marcel Dekker Inc., New York and Basel, 1989. Iontophoretic transdermal delivery system typically include a first (donor) electrode containing an electrolytically available active compound within a suitable vehicle or carrier, a second (passive) electrode and a power source, the first and second electrodes each being in electrically conductive communication with the power source. The first and second electrodes are being adapted for spaced apart physical contact with the skin whereby, in response to a current provided by the power source through the electrodes, a therapeutic amount of the active compound is administered through the skin to a patient.

Suitable pharmaceutical carriers include those well known in the art of pharmacy for the preparation of topical formulations such as glycols and glycol ethers, polyethylene glycol, propylene glycol, glycerol and glycerol ethers, lower alcohols such as ethanol or isopropanol, water, non-volatile fatty alcohols, e.g. cetostearyl alcohol and cetyl alcohol, N-methylpyrrolidone, vegetable and animal oils, sesame oil, olive oil, wood alcohol ointments, vaseline and paraffin, cellulose derivatives, e.g. methylcellulose, hydroxy propylmethyl cellulose (HPMC) or carboxymethyl cellulose, or mixtures thereof.

Suitable skin penetration enhancers include those well known in the art, for example, $C_2$–$C_4$ alcohols such as ethanol and isopropanol; surfactants, e.g. anionic surfactants such as salts of fatty acids of 5 to 30 carbon atoms, e.g. sodium lauryl sulphate and other sulphate salts of fatty acids, cationic surfactants such as alkylamines of 8 to 22 carbon atoms, e.g. oleylamine, and nonionic surfactants such as polysorbates and poloxamers; aliphatic monohydric alcohols of 8 to 22 carbon atoms such as decanol, lauryl alcohol, myristyl alcohol, palmityl alcohol, linolenyl alcohol and oleyl alcohol; fatty acids of 5 to 30 carbon atoms such as oleic acid, stearic acid, linoleic acid, palmitic acid, myristic acid, lauric acid and capric acid and their esters such as ethyl caprylate, isopropyl myristate, methyl laurate, hexamethylene palmitate, glyceryl monolaurate, polypropylene glycol monolaurate and polyethylene glycol monolaurate; salicylic acid and its derivatives; alkyl methyl sulfoxides such as decyl methyl sulfoxide and dimethyl sulfoxide; 1-substituted azacycloalkan-2-ones such as 1-dodecylazacyclo-heptan-2-one sold under the trademark AZONE; amides such as octylamide, oleicamide, hexamethylene lauramide, lauric diethanolamide, polyethylene glycol 3-lauramide, N,N-diethyl-m-toluamide and crotamiton; and any other compounds compatible with levosimendan and the packages and having transdermal permeation enhancing activity.

The preparation according to the invention may also include an antimicrobial agent, a preservative, an antioxidant and a pH-controlling agent and other additives known in the art.

Preferred administration rate of levosimendan in the transdermal delivery is within the range of about 1–1000 μg/h through a skin area of about 2–100 $cm^2$. The daily dose of levosimendan to man is within the range of about 0.1 to 500 mg, preferably 0.5 to 10 mg depending on the age, body weight and condition of the patient. The amount of drug delivered into the skin can be controlled by a number of factors including skin patch size, degree of drug loading, the use of rate controlling membranes, permeation enhancers etc.

EXPERIMENTS

Permeation Experiments

Transdermal penetration of levosimendan across human skin in vitro was studied with side-by-side diffusion chambers (DC-100, Crown Glass Co., Somerville, N.J.) at 25° C. The receiver phase (3 ml) consisted of blank sodium phosphate buffer (pH 5.0). Each studied saturated levosimendan solution (3 ml) was added to the donor side. Levosimendan permeation from the gel-formulation was studied with Franz -diffusion chambers (DC-400, Crown Glass Co., Somerville, N.J.) at 25° C. The volume of donor and receiver phases were 1 ml and 5 ml, respectively. Samples were withdrawn up to 72 h at fixed intervals and levosimendan concentration in samples was determined by HPLC (Beckman System Gold, Beckman Instruments Inc., CA). The HPLC column used was LiChrosorb RP-18 (7 μm, 250 mm×4 mm), and the mobile phase was 55% of methanol and 45% of sodium phosphate buffer at pH 2,1. Detection wavelength was 360 nm and flow rate was 1.2 ml per min. Trans-dermal flux of levosimendan (μg/h per $cm^2$) across the skin was calculated using linear regression of the straight-line portion of drug permeation vs. time curve, and dividing by the surface area of the skin (0.64 $cm^2$).

The gel formulation of levosimendan was prepared from hydroxy propylmethyl cellulose (HPMC) (2.5% m/V, average M.W. 100.000; Aldrich Chemical Co., Steinheim, Germany), and ethanol (10%) and sodium lauryl sulphate (0.01%) were added to the gel. The permeation results show that levosimendan permeation across human skin in vitro was practically the same from the solution and from the gel prepared from the same solution.

The permeation results are shown in Table 1.

TABLE 1

Permeation of levosimendan across human skin in vitro. Donor formulations buffered to pH 5 with sodium phosphate buffer. SLS = sodium lauryl sulphate, PG = propylene glycol, OA = oleic acid. % = % m/V.

| Donor formulation | Conc. mg/ml | pH | Flux ± SD μg/$cm^2$h | Lag time h |
|---|---|---|---|---|
| water + 90% ethanol | 3.66 | 5.0 | 7.05 ± 1.11 | 15 |
| water + 40% ethanol | 1.73 | 5.0 | 0.87 ± 0.21 | 15 |
| water + 10% ethanol + 0.01% SLS | 0.061 | 5.0 | 0.43 ± 0.09 | 15 |
| water + 10% ethanol + 0.01% SLS HPMC-gel (2.5%) | 0.061 | 5.0 | 0.48 ± 0.15 | 15 |
| water + 10% ethanol + 40% PG + 5% OA | 1.19 | 5.0 | 16.0 ± 1.62 | 15 |
| water + 0.1% SLS | 0.061 | 5.0 | 5.25 ± 0.96 | 20 |
| water + 1% SLS | 0.49 | 5.0 | 25.38 ± 5.46 | 20 |

Permeation from Iontophoretic Device

Electrodes for iontophoresis were prepared from silver wire and silver chloride (Aldrich-Chemie, Steinheim, Germany). Direct current (0.5 mA/$cm^2$) during iontophoresis was delivered by HP 6181C DC current source (Hewlett-Packard, CA) from the electrodes to the diffusion chambers via salt bridges. Salt bridges were prepared by injecting 1 M NaCl-gel (3% agar) inside plastic tubing (diameter 4 mm, length 15 cm). Salt bridges prevented direct contact and possible reactions of levosimendan with Ag/AgCl-electrodes. HEPES-buffer at pH 7.4 was used in the receiver phase. Saturated levosimendan solution (3 ml) in HEPES-buffer (pH 7.4) was added to the donor side. AgCl-cathode was connected via the salt bridge to the donor solution. Positive silver anode was connected via the salt bridge to the receiver solution. The chambers were connected in series as constant DC-current was used. The Ag/AgCl-electrodes could be used continuously for 12 h. The results of this experiment are summarized in Table 2.

TABLE 2

Penetration of levosimendan across human skin in vitro by iontophoresis (constant current 0.5 mA/$cm^2$).

| Donor solution | Conc. mg/ml | pH | Flux ± SD μg/$cm^2$h | Lag time h |
|---|---|---|---|---|
| HEPES-buffer | 0.41 | 7.4 | 2.87 ± 0.57 | 2 |

What is claimed is:

1. A transdermal preparation, comprising, as a therapeutically active ingredient, (−)-[[4-(1,4,5,6-tetrahydro-4-methyl-6-oxo-3-pyridazinyl)phenyl]-hydrazono] propanedinitrile or a pharmaceutically acceptable salt thereof.

2. The preparation according to claim 1, wherein the preparation is in the form of an ointment, an emulsion, a lotion, a solution, a gel, a cream, or a patch.

3. The preparation according to claim 1, wherein the preparation is a transdermal delivery system, comprising (a) a drug impermeable backing layer and (b) an adhesive layer, wherein the active ingredient is dispersed in the adhesive layer.

4. The preparation according to claim 1, wherein the preparation is a transdermal delivery system, comprising (a)

a drug impermeable backing layer; (b) an adhesive layer; and (c) a matrix layer, in which the active ingredient is dispersed.

5. The preparation according to claim 4, wherein the matrix layer is made of a polymer material.

6. The preparation according to claim 1, wherein the preparation is an iontophoretic transdermal delivery system.

7. A method (for treating heart failure) comprising administering transdermally to a subject in need of such treatment a therapeutically effective amount of (−)-[[4-(1,4,5,6-tetrahydro-4-methyl-6-oxo-3-pyridazinyl)phenyl]-hydrazono]propanedinitrile or a pharmaceutically acceptable salt thereof.

8. The preparation according to claim 1, wherein the preparation is a transdermal delivery system, comprising (a) a drug impermeable backing layer;

(b) an adhesive layer;

(c) a drug permeable membrane, wherein the membrane is positioned relative to the backing layer so that at least one drug reservoir compartment is defined between the membrane and the backing layer; and (d) the active ingredient or a composition thereof within the drug reservoir.

9. The method according to claim 7, wherein (−)-[[4-(1,4,5,6-tetrahydro-4-methyl-6-oxo-3-pyridazinyl)phenyl] hydrazono]propanedinitrile or a pharmaceutically acceptable salt thereof is administered from about 1 $\mu$g/h to about 1000 $\mu$g/h.

10. The method according to claim 9, wherein (−)-[[4-(1,4,5,6-tetrahydro-4-methyl-6-oxo-3-pyridazinyl)phenyl] hydrazono]propanedinitrile or a pharmaceutically acceptable salt thereof is administered through a skin area of from about 2 $cm^2$ to about 100 $cm^2$.

11. The method according to claim 7 wherein the dose of (−)-[[4-(1,4,5,6-tetrahydro-4-methyl-6-oxo-3-pyridazinyl) phenyl]hydrazono]propanedinitrile or a pharmaceutically acceptable salt thereof administered is from about 0.1 mg to about 500 mg per day.

12. The method according to claim 11, wherein the dose is from about 0.5 mg to about 10 mg per day.

* * * * *

UNITED STATES PATENT AND TRADEMARK OFFICE
CERTIFICATE OF CORRECTION

PATENT NO.    : 6,183,771 B1
DATED         : February 6, 2001
INVENTOR(S)   : Arto Urtti et al.

It is certified that error appears in the above-identified patent and that said Letters Patent is hereby corrected as shown below:

<u>Title page,</u>
Item [57], ABSTRACT,
Line 2, "tetahydro" should read -- tetrahydro --.

<u>Column 5,</u>
Line 8, "(for treating heart failure)" should read -- for treating heart failure, --.

<u>Column 6,</u>
Line 13, after "claim 7", insert a comma.

Signed and Sealed this

Twentieth Day of January, 2004

JON W. DUDAS
*Acting Director of the United States Patent and Trademark Office*